US008632664B2

(12) United States Patent
Macfie et al.

(10) Patent No.: US 8,632,664 B2
(45) Date of Patent: Jan. 21, 2014

(54) TEST METER FOR USE WITH A DUAL CHAMBER, MULTI-ANALYTE TEST STRIP WITH OPPOSING ELECTRODES

(75) Inventors: Gavin Macfie, Inverness (GB); Graeme Webster, Inverness (GB); Marco F. Cardosi, Croy (GB); Christopher Philip Leach, Inverness (GB); Steven Setford, Fortrose (GB); Selwayan Saini, Culbokie (GB)

(73) Assignee: LifeScan Scotland Limited, Inverness (GB)

( * ) Notice: Subject to any disclaimer, the term of this patent is extended or adjusted under 35 U.S.C. 154(b) by 604 days.

(21) Appl. No.: 12/606,496

(22) Filed: Oct. 27, 2009

(65) Prior Publication Data

US 2011/0094882 A1 Apr. 28, 2011

(51) Int. Cl.
*G01N 27/327* (2006.01)

(52) U.S. Cl.
USPC .................. 204/403.03; 435/25; 600/347

(58) Field of Classification Search
USPC ......... 204/403.01–403.15, 229.8–230.1, 267; 205/775.5, 778, 787, 792; 422/68.1, 422/82.01; 435/4, 11, 14, 25–28; 600/345–347
See application file for complete search history.

(56) References Cited

U.S. PATENT DOCUMENTS

| | | | |
|---|---|---|---|
| 5,264,103 A | 11/1993 | Yoshioka et al. | |
| 5,708,247 A | 1/1998 | McAleer et al. | |
| 5,951,836 A | 9/1999 | McAleer et al. | |
| 6,241,862 B1 | 6/2001 | McAleer et al. | |

(Continued)

FOREIGN PATENT DOCUMENTS

| | | |
|---|---|---|
| CN | 1858591 A | 11/2006 |
| GB | 2337122 A | 11/1999 |
| WO | WO 2005/098431 A1 | 10/2005 |
| WO | WO 2008/044530 A1 | 4/2008 |

OTHER PUBLICATIONS

Extended European Search Report dated Feb. 7, 2011, corresponding to Application No. 10251846.1.

(Continued)

*Primary Examiner* — J. Christopher Ball

(57) ABSTRACT

A test meter for use with a dual-chamber, multi-analyte test strip includes a test strip receiving module and a signal processing module. The test strip receiving module has a first electrical connector configured for contacting a first analyte contact pad of a first working electrode of the test strip; a second electrical connector configured for contacting a second analyte contact pad of a second working electrode of the test strip, a third electrical connector configured for contacting a first counter/reference contact pad of a first counter/reference electrode layer of the test strip, and a fourth electrical connector configured for contacting a second counter/reference contact pad of a second counter/reference electrode layer of the test strip. The signal processing module is configured to receive a first signal via the first electrical connector and the third electrical connector and employ the first signal for the determination of a first analyte (such as glucose) in a bodily fluid sample (for example, whole blood sample) applied to the dual-chamber, multi-analyte test strip. Moreover, the signal processing module is also configured to receive a second signal via the second electrical connector and fourth electrical connector and employ the second signal for the determination of a second analyte (e.g., a ketone analyte) in the bodily fluid sample applied to the dual-chamber, multi-analyte test strip. Furthermore, the third and fourth electrical contacts provide contact in an opposing manner.

10 Claims, 6 Drawing Sheets

(56) References Cited

U.S. PATENT DOCUMENTS

| | | |
|---|---|---|
| 6,284,125 B1 | 9/2001 | Hodges et al. |
| 7,431,820 B2 | 10/2008 | Hodges |
| 2003/0068666 A1 | 4/2003 | Zweig |
| 2005/0003523 A1 | 1/2005 | Anaokar et al. |
| 2008/0202928 A1 | 8/2008 | Hyun et al. |
| 2009/0020438 A1 | 1/2009 | Hodges |
| 2009/0078588 A1 | 3/2009 | Lin et al. |
| 2010/0096276 A1* | 4/2010 | Kojima et al. ............. 205/777.5 |

OTHER PUBLICATIONS

Extended European Search Report dated Feb. 3, 2011, corresponding to Application No. 10251847.9.

* cited by examiner

US 8,632,664 B2

TEST METER FOR USE WITH A DUAL CHAMBER, MULTI-ANALYTE TEST STRIP WITH OPPOSING ELECTRODES

BACKGROUND OF THE INVENTION

1. Field of the Invention

The present invention relates, in general, to medical devices and, in particular, to analyte test strips, test meters and related methods.

2. Description of Related Art

The determination (e.g., detection and/or concentration measurement) of an analyte in a fluid sample is of particular interest in the medical field. For example, it can be desirable to determine glucose, ketones, cholesterol, acetaminophen and/or HbAlc concentrations in a sample of a bodily fluid such as urine, blood or interstitial fluid. Such determinations can be achieved using analyte test strips, based on, for example, photometric or electrochemical techniques, along with an associated test meter.

Typical electrochemical-based analyte test strips employ a working electrode along with an associated counter/reference electrode and enzymatic reagent to facilitate an electrochemical reaction with a single analyte of interest and, thereby, determine the concentration of that single analyte. For example, an electrochemical-based analyte test strip for the determination of glucose concentration in a blood sample can employ an enzymatic reagent that includes the enzyme glucose oxidase and the mediator ferricyanide. Such conventional analyte test strips are described in, for example, U.S. Pat. Nos. 5,708,247; 5,951,836; 6,241,862; and 6,284,125; each of which is hereby incorporated in full by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

FIGS. 2A-2K are simplified top views of the first insulating layer, first electrically conductive layer, first analyte reagent layer, first patterned spacer layer, first counter/reference electrode layer, counter/reference insulating layer, second counter/reference electrode layer, second patterned spacer layer, second analyte reagent layer, second electrically conductive layer, and second insulating layer, respectively, of the dual chamber, multi-analyte test strip of FIG. 1;

DETAILED DESCRIPTION OF ILLUSTRATIVE EMBODIMENTS

Figure 1:
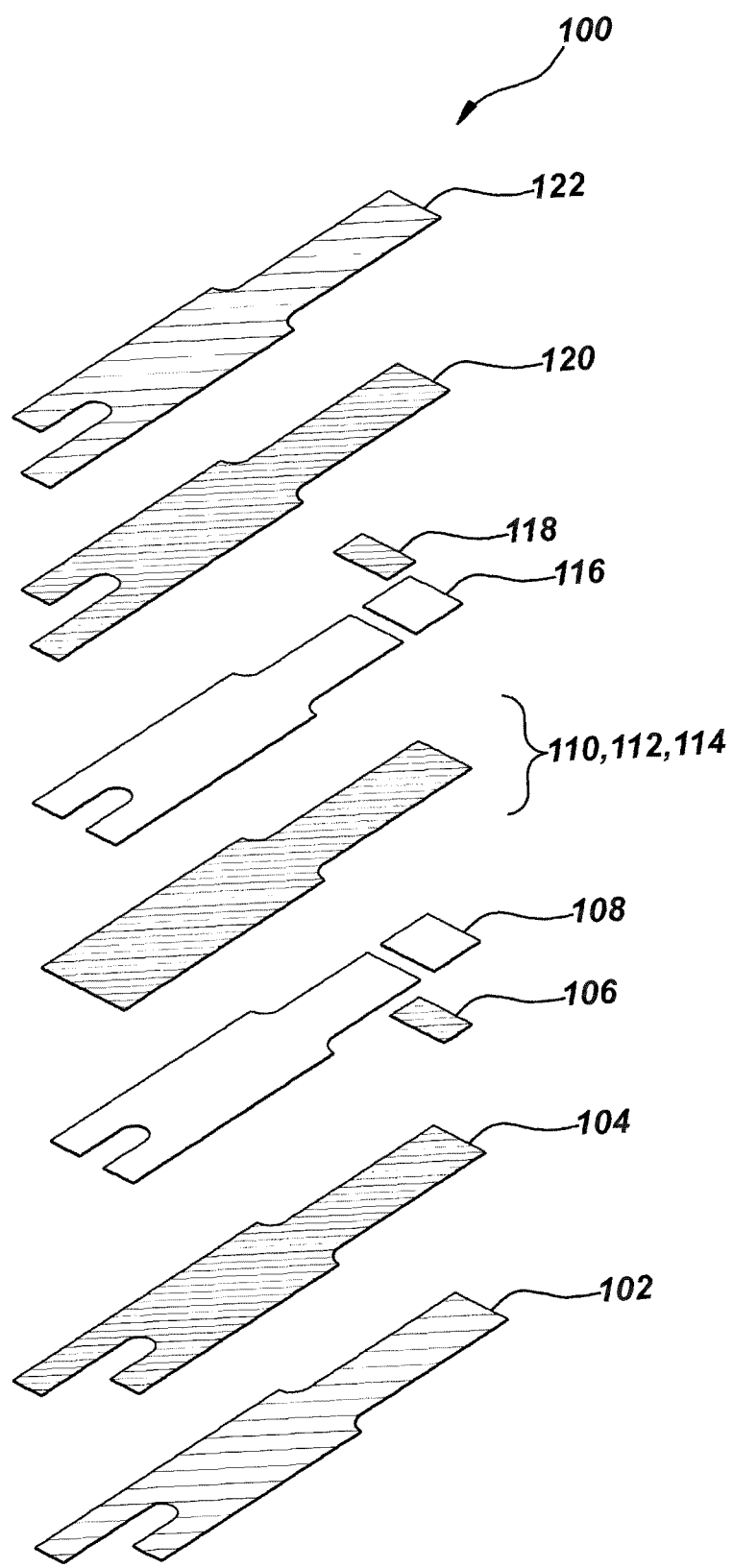
FIG. 1 is a simplified exploded, perspective depiction of a dual chamber, multi-analyte test strip according to an embodiment of the present invention.
Figure 2A:
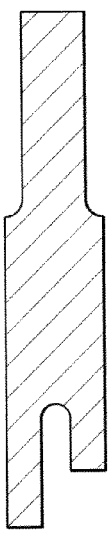
Figure 2B:
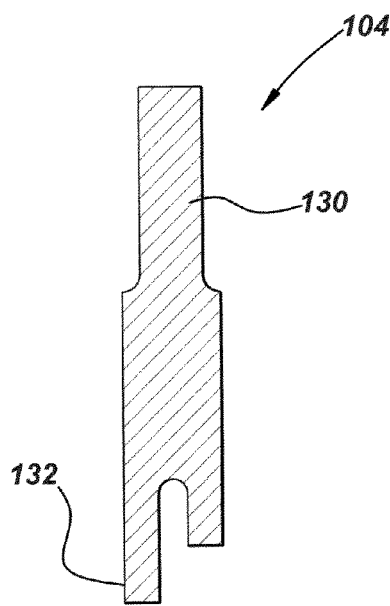
Figure 2C:
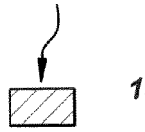
Figure 2D:
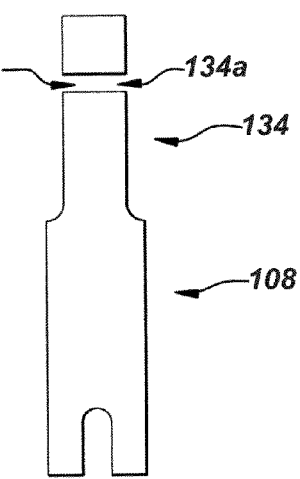
Figure 2E:
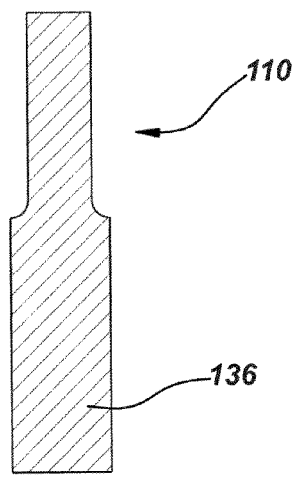
Figures 2F, 2G, 2H:
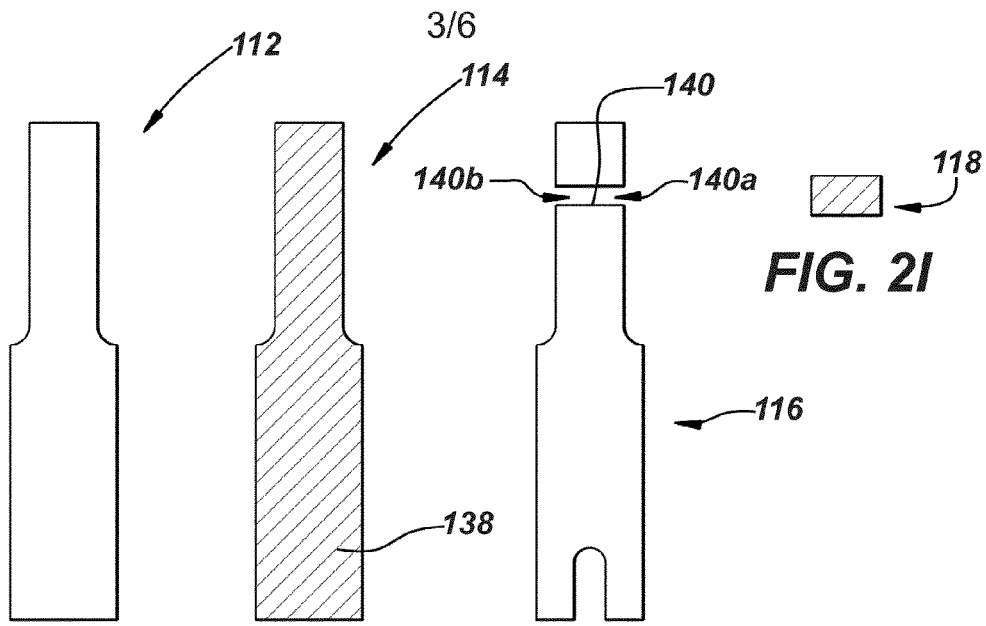
Figures 2J, 2K:
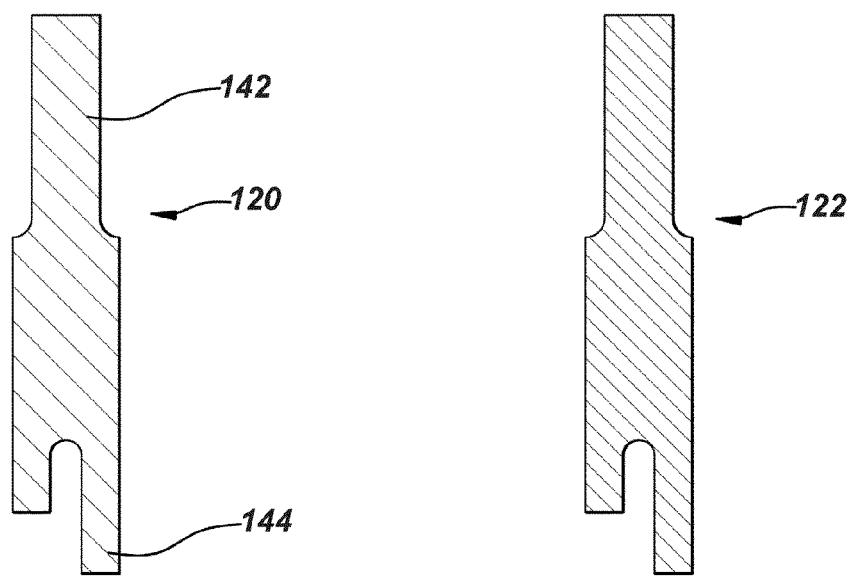

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Dual chamber, multi-analyte test strips (also referred to herein simply as test strips) according to embodiments of the present invention include a first insulating layer, a first electrically conductive layer (with a first working electrode and a first analyte contact pad) disposed on the first insulating layer, and a first patterned spacer layer. The first patterned spacer layer is positioned above the first electrically conductive layer and has a first sample-receiving chamber, with first and second end openings, defined therein. The first sample-receiving chamber overlies the first working electrode. The test strip also includes a first counter/reference electrode layer that is exposed to the first sample receiving chamber and is configured in an opposing (i.e., co-facial) relationship to the first working electrode. The first counter/reference electrode layer has a first counter/reference contact pad.

The test strip further includes a counter/reference insulating layer disposed over the first counter/reference electrode layer and a second counter/reference electrode layer (with a second counter/reference contact pad) disposed on the counter/reference insulating layer. Also included in the test strip is a second patterned spacer layer that is positioned above the second counter/reference electrode layer. The second patterned spacer layer has a second sample-receiving chamber, with first and second end openings, defined therein. The test strip additionally has a second electrically conductive layer (with a second working electrode and a second analyte contact pad), disposed above the second patterned spacer layer, a second insulating layer disposed above the second electrically conductive layer, a first analyte reagent layer disposed on the first working electrode within the first sample-receiving chamber, and a second analyte reagent layer disposed on the second working electrode within the second sample-receiving chamber. The second counter/reference electrode layer is exposed to the second sample receiving chamber and is in an opposing (co-facial) relationship to the second working electrode.

Dual chamber, multi-analyte test strips according to embodiments of the present invention are beneficial in that, for example, a plurality of non-identical analytes (e.g., the analyte glucose and the ketone analyte 3-hydroxybutyrate) can be determined in a single bodily fluid sample (such as a single whole blood sample) applied to the test strips. In addition, since the dual chamber, multi-analyte test strips have two separate sample-receiving chambers, the potential for deleterious cross-contamination between analyte reagents, cross-contamination of reaction products and/or byproducts, and/or cross-electrical interference during the determination of the two analytes is eliminated. Moreover, since the first counter/reference electrode is in an opposing (i.e., co-facial) relationship to the first working electrode and the second counter/reference electrode layer is also in an opposing (i.e., co-facial) relationship to the second working electrode, the dual chamber, multi-analyte test strips are beneficially small in overall size and have a small sample-receiving chambers. Moreover, dual chamber, multi-analyte test strips according to embodiments of the present invention can be manufactured using conventional, simple and relatively inexpensive web-based techniques.

Figure 3:
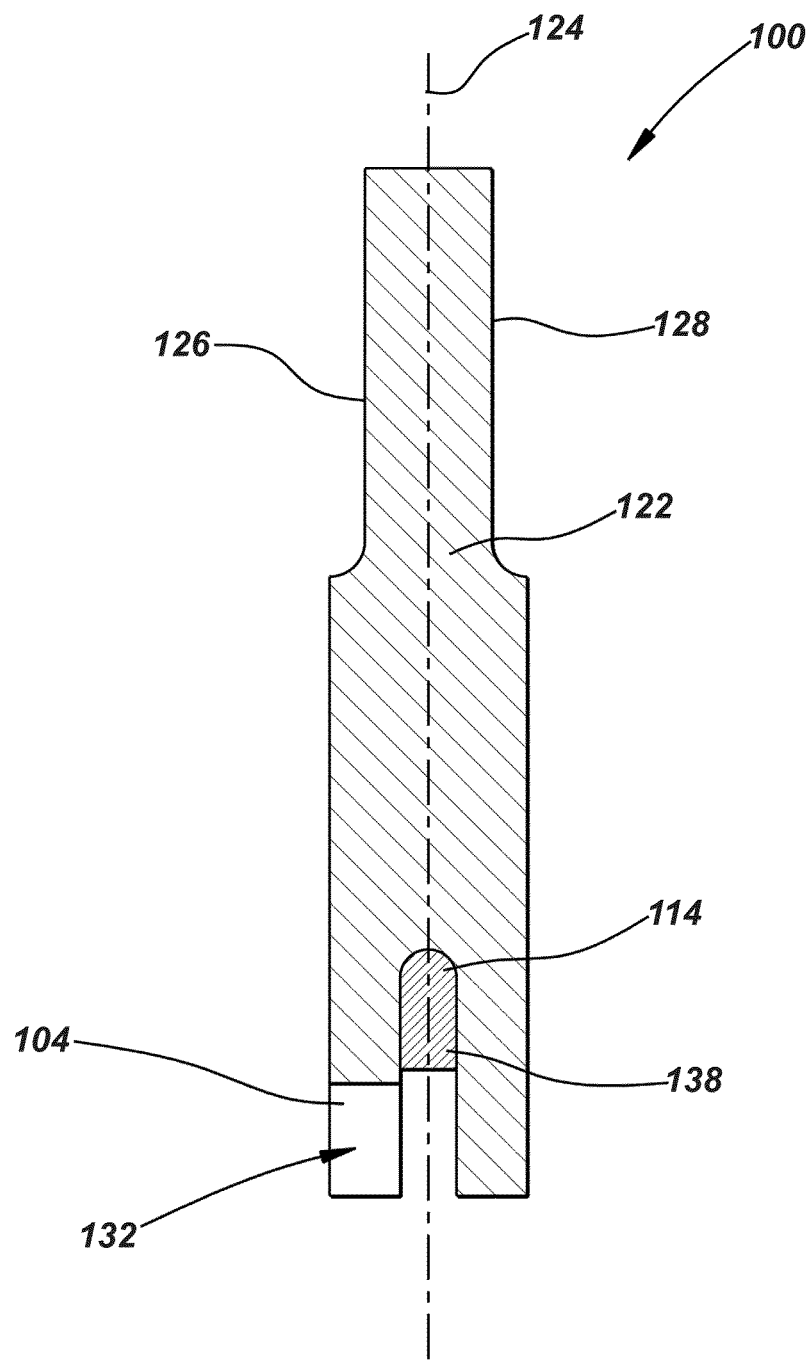
FIG. 3 is a simplified top view of the dual chamber, multi-analyte test strip of FIG. 1.

FIG. 1 is a simplified perspective, exploded depiction of a dual chamber, multi-analyte test strip 100 according to an embodiment of the present invention. FIGS. 2A-2K are simplified top views of a first insulating layer 102, first electrically conductive layer 104, first analyte reagent layer 106, first patterned spacer layer 108, first counter/reference electrode layer 110, counter/reference insulating layer 112, second counter/reference electrode layer 114 (it should be noted that for simplicity layers 110, 112, and 114 are shown as a single layer in FIG. 1 and more accurately as separate layers in FIGS. 2E-2G), second patterned spacer layer 116, second analyte reagent layer 118, second electrically conductive layer 120, and second insulating layer 122 of dual chamber, multi-analyte test strip 100. FIG. 3 is a simplified top view of dual chamber, multi-analyte test strip 100.

Figure 4A:
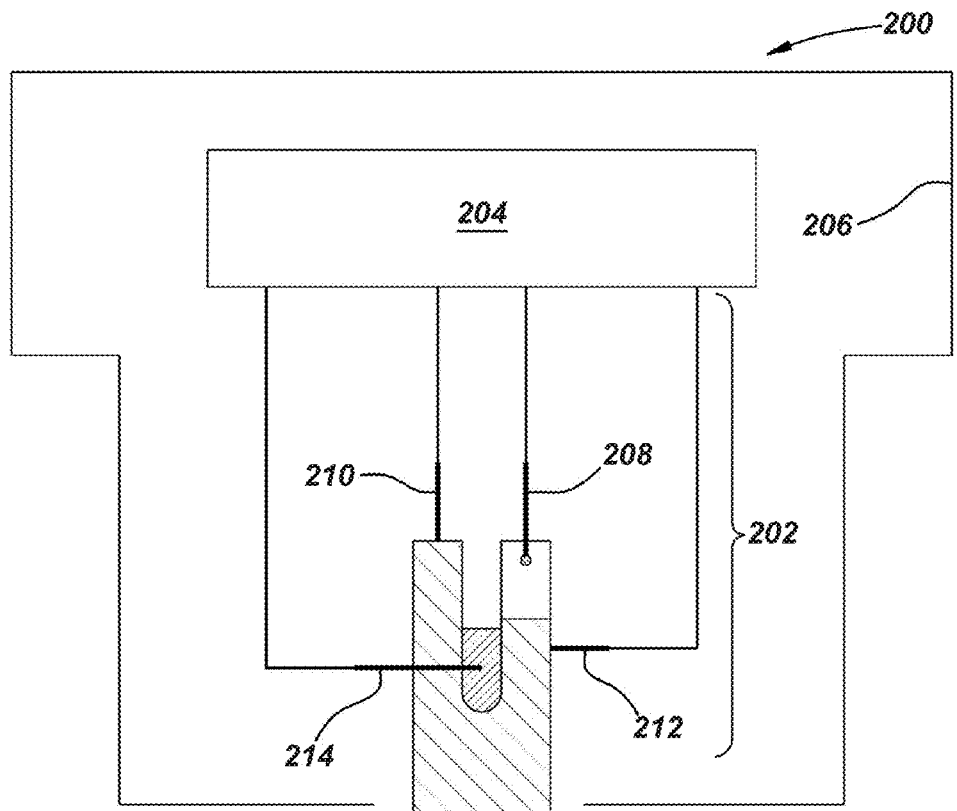
FIG. 4A is a simplified depiction of the dual chamber, multi-analyte test strip of FIGS. 1-3 in use with a test meter according to an embodiment of the present invention.
Figure 4B:
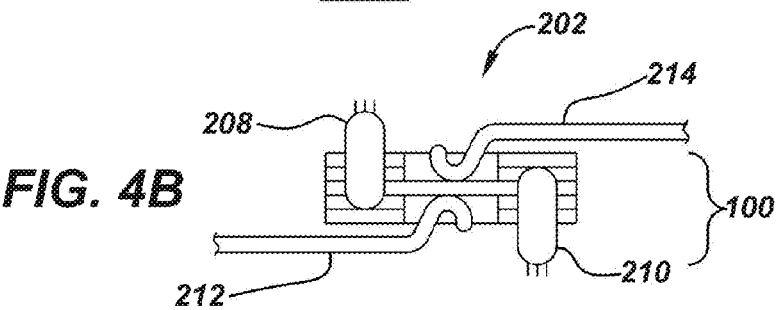
FIG. 4B is a simplified depiction end view of the dual chamber, multi-analyte test strip and test meter electrical connectors of the FIG. 4A.

Referring to FIG. 1, FIGS. 2A through 2K and FIG. 3, dual chamber, multi-analyte test strip 100 is configured for use with a test meter (described further herein, for example, with respect to the embodiment of FIGS. 4A and 4B) and has a longitudinal axis 124 (depicted by a broken line in FIG. 3), a left lateral edge 126 and a right lateral edge 128.

Dual chamber, multi-analyte test strip 100 includes first insulating layer 102, with first electrically conductive layer 104 disposed thereon. First electrically conductive layer 104 includes a first working electrode 130 with a first analyte contact pad 132 (see FIG. 2B in particular). First patterned spacer layer 108 of dual chamber, multi-analyte test strip 100 is disposed above first electrically conductive layer 104 (see FIG. 1 in particular), with the patterned spacer layer defining a first sample-receiving chamber 134 therein that overlies first working electrode 130. In addition, first sample-receiving chamber 134 has a first end opening 134a and a second end opening 134b.

First counter/reference electrode layer 110 of dual chamber, multi-analyte test strip 100 overlies, and is exposed to, first sample-receiving chamber 134 and is configured in an opposing relationship to first working electrode 130 (see FIG. 1). In addition, first counter/reference electrode layer 110 has a counter/reference electrode contact pad 136 (see FIG. 2E in particular).

Dual chamber, multi-analyte test strip 100 also includes a counter/reference insulating layer 112 disposed over first counter/reference electrode layer 110. Second counter/reference electrode layer 114 is disposed over counter/reference insulating layer 112 and has a second counter/reference contact pad 138 (see FIGS. 2G and 3 in particular). Counter/reference insulating layer 112 provides electrical insulation between first counter/reference electrode layer 110 and second counter/reference electrode layer 114.

Dual chamber, multi-analyte test strip 100 further includes a second patterned spacer layer 116 that is positioned above second counter/reference electrode layer 114 and that has a second sample-receiving chamber 140 defined therein. Second sample-receiving chamber 140 has a first end opening 140a and a second end opening 140b.

A second electrically conductive layer 120 of dual chamber, multi-analyte test strip 100 is disposed above second patterned spacer layer 116. Second electrically conductive layer 120 includes a second working electrode 142 with a second analyte contact pad 144 (see FIG. 2J).

A second insulating layer 122 of dual chamber, multi-analyte test strip 100 is disposed above second electrically conductive layer 120. Dual chamber, multi-analyte test strip 100 also has a first analyte reagent layer 106 (such as a glucose reagent layer) disposed on at least a portion of the first working electrode 130 within the first sample-receiving chamber 134 and a second analyte reagent layer 118 (for example, a ketone reagent layer) disposed on at least a portion of second working electrode 142 within second sample-receiving chamber 140.

In dual chamber, multi-analyte test strip 100, second sample-receiving chamber 140 overlies the second working electrode 142 and second counter/reference electrode layer 114 is exposed to the second sample receiving chamber 140 and configured in an opposing (i.e., co-facial) relationship to the second working electrode 142.

Dual chamber, multi-analyte test strip 100 is configured such that first end opening 134a of first sample-receiving chamber 134 and first end opening 140a of second sample-receiving chamber 140 are aligned on right lateral edge 128. In other words, first end opening 134a is directly below first end opening 140a and the two openings are only separated by the thickness of the first and second counter/reference electrode layers and counter/reference insulating layer. This alignment provides for a single bodily fluid sample applied on right lateral edge 128 to readily enter (via capillary action) both the first and second sample-receiving chambers with the second end opening 134b and second end opening 140b serving as vents. However, since second end opening 134b is aligned with second end opening 140b on the left lateral edge 126, a single blood bodily fluid sample can alternatively be applied to the left lateral edge and thereby enter (via capillary action) the first and second sample-receiving chambers via the second end opening 134b and second end opening 140b with first end opening 134a and first end opening 140a acting as vents.

In the embodiment of FIGS. 1, 2A-2K and 3, first analyte contact pad 132, first counter/reference contact pad 136, second analyte contact pad 144 and second counter/reference contact pad 138 are configured for operational electrical contact with electrical connectors of a test meter. An exemplary but non-limiting connection of such pads and electrical connectors is illustrated and described elsewhere herein with respect to FIGS. 4A and 4B.

First insulating layer 102, counter/reference insulating layer 112 and second insulating layer 122 can be formed, for example, of a suitable electrically insulating plastic (e.g., PET, PETG, polyimide, polycarbonate, polystyrene), silicon, ceramic, or glass material. For example, the first and second insulating layers and counter/reference insulating layer can be formed from a 7 mil polyester substrate.

In the embodiment of FIGS. 1, 2A-2K and 3, first working electrode 130 and first counter/reference electrode layer 110, along with first analyte reagent layer 106, are configured for the electrochemical determination of a first analyte concentration in a bodily fluid sample (such as glucose in a whole blood sample) using any suitable electrochemical-based technique known to one skilled in the art. Furthermore, second working electrode 142 and second counter/reference electrode layer 114, along with second analyte reagent layer 118, are configured for the electrochemical determination of a second analyte concentration in the same bodily fluid sample (such as the concentration of the ketone 3-hydroxybutyrate). In this scenario, the first analyte is determined in a portion of the single bodily fluid sample that enters the first sample-receiving chamber and the second analyte is determined in a portion of the single bodily fluid sample that enters the second sample-receiving chamber.

First electrically conductive layer 104 and second electrically conductive layer 120 can be formed of any suitable conductive material such as, for example, gold, palladium, carbon, silver, platinum, tin oxide, iridium, indium, or combinations thereof (e.g., indium doped tin oxide). Moreover, any suitable technique can be employed to form first electrically conductive layer 104 and second electrically conductive layer 120 including, for example, sputtering, evaporation, electro-less plating, screen-printing, contact printing, or gravure printing. For example, first electrically conductive layer 104 and second electrically conductive layer 120 can be a palladium layers formed by sputtering Pd onto first insulating layer 102 and second insulating layer 122, respectively. Such a Pd layer can have, for example, an electrical sheet resistance in the range of 8-12 ohm/cm$^2$ and a thickness of approximately 60 nm.

First counter/reference electrode layer 110 can, for example, be a gold layer that is sputter coated on the underside of counter/reference insulating layer 112 using conventional techniques known in the art. Similarly, second counter/reference electrode layer 114 can, for example, be a gold layer that is sputter coated on the topside of counter/reference insulating layer 112 using conventional techniques known in the art. Such a gold layer can have, for example, an electrical sheet resistance in the range of 8 to 12 ohm cm$^2$ and a thickness of approximately 30 nm.

First patterned spacer layer 108 of dual chamber, multi-analyte test strip 100 is configured to bind together first insulating layer 102 (with first electrically conductive layer 104 thereon) and counter/reference insulating layer 112 (with first counter/reference electrode layer 110 on the underside thereof and second counter/reference electrode layer 114 on the topside thereof). Second patterned spacer layer 116 of dual chamber, multi-analyte test strip 100 serves to bind together second insulating layer 122 (with second electrically conductive layer 120 thereon) and second counter/reference electrode layer 114.

Patterned spacer layers 108 and 116 can be, for example, a 95 μm thick, double-sided pressure sensitive adhesive layers, heat activated adhesive layers, or thermo-setting adhesive plastic layers. Patterned spacer layers 108 and 116 can have, for example, a thickness in the range of from about 1 micron to about 500 microns, preferably between about 10 microns and about 400 microns, and more preferably between about 40 microns and about 200 microns.

First analyte reagent layer 106 of dual chamber, multi-analyte test strip 100 can be any suitable mixture of reagents known to those of skill in the art that selectively reacts with a first analyte, such as, for example glucose, in a bodily fluid sample to form an electroactive species, which can then be quantitatively measured at the first working electrode of dual chamber, multi-analyte test strips according to embodiments of the present invention. Therefore, first analyte reagent layer 106 includes at least an enzyme and a mediator. Examples of suitable mediators include, for example, ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. First analyte reagent layer 106 can be applied using any suitable technique.

Second analyte reagent layer 118 of dual chamber, multi-analyte test strip 100 can be any suitable mixture of reagents known to those of skill in the art that selectively reacts with a second analyte such as, for example the ketone 3-hydroxybutyrate, in a bodily fluid sample to form an electroactive species, which can then be quantitatively measured at the second working electrode of dual chamber multi-analyte test strips according to embodiments of the present invention. Therefore, second analyte reagent layer 118 includes at least an enzyme and a mediator. Second analyte reagent portion 118 can be applied using any suitable technique. It should be noted that the first and second analytes are dissimilar. In other words, the first and second analytes are not the same chemical species. Therefore, two different analytes are determined by dual chamber, multi-analyte test strips according to the present invention.

When the second analyte is the ketone 3-hydroxybutyrate, the mediator can be, for example, a mixture of potassium ferricyanide and NAD and the enzyme can be, for example, a mixture of diaphorase and hydroxybutyrate dehydrogenase.

Once apprised of the present invention, one skilled in the art will recognize that first analyte reagent layer 106 and second analyte reagent layer 118 can, if desired, also contain suitable buffers (such as, for example, Tris HCl, Citraconate, Citrate and Phosphate buffers), surfactants (for example, Tritoan X100, Tergitol NP &, PLuronic F68, Betaine and Igepal surfactants), thickeners (including, for example, hydroxyethylcelulose, HEC, carboxymethylcellulose, ethycellulose and alginate thickeners) and other additives as are known in the field.

It should be noted that in the embodiment of FIGS. 1-3, first analyte contact pad 132 and the second analyte contact pad 144 are exposed on opposite sides of dual chamber, multi-analyte test strip 100. In other words, in the perspective of FIG. 1, first analyte contact pad 132 is exposed from the top side of dual chamber, multi-analyte test strip 100 and second analyte contact pad 144 is exposed from the bottom side of dual chamber, multi-analyte test strip 100. Such a configuration facilitates the establishment of a secure and robust electrical connection by electrical connectors of a test meter.

Test meters for use with a dual-chamber, multi-analyte test strip according to embodiments of the present invention include a test strip receiving module and a signal processing module. The test strip receiving module has a first electrical connector configured for contacting a first analyte contact pad of a first working electrode of the test strip; a second electrical connector configured for contacting a second analyte contact pad of a second working electrode of the test strip, a third electrical connector configured for contacting a first counter/reference contact pad of a first counter/reference electrode layer of the test strip, and a fourth electrical connector configured for contacting a second counter/reference contact pad of a second counter/reference electrode layer of the test strip.

The signal processing module of the test meter is configured to receive a first signal via the first electrical connector and the third electrical connector and employ the first signal for the determination of a first analyte (such as glucose) in a bodily fluid sample (for example, a whole blood sample) applied to the dual-chamber, multi-analyte test strip. Moreover, the signal processing module is also configured to receive a second signal via the second electrical connector and fourth electrical connector and employ the second signal for the determination of a second analyte (e.g., a ketone analyte) in the bodily fluid sample applied to the dual-chamber, multi-analyte test strip. Furthermore, the third electrical connector is configured to contact the first counter/reference contact pad in an opposing manner with respect to the contact of the fourth electrical connector and the second counter/reference contact pad.

FIG. 4A is a simplified depiction of dual chamber, multi-analyte test strip 100 in use with a test meter 200 according to an embodiment of the present invention. In FIG. 4A, dashed lines indicate certain features hidden from view in the perspective of FIG. 4A. FIG. 4B is a simplified depiction end view of dual chamber, multi-analyte test strip 100 and test meter electrical connectors of test meter 200. Test meter 200 includes a test strip receiving module 202 and a signal processing module 204 within a case 206.

The test strip receiving module 202 has a first electrical connector 208 configured for contacting the first analyte contact pad of the test strip, a second electrical connector 210 configured for contacting a second analyte contact pad of the test strip, a third electrical connector 212 configured for contacting a first counter/reference contact pad of the test strip, and a fourth electrical connector 214 configured for contacting a second counter/reference contact pad of the test strip.

Signal processing module 204 is configured to receive a first signal via first electrical connector 208 and third electrical connector 212 and employ the first signal for the determination of a first analyte in a bodily fluid sample applied to the dual-chamber, multi-analyte test strip. In addition, signal processing module 204 is also configured to receive a second signal via second electrical connector 210 and fourth electrical connector 214 and employ the second signal for the determination of a second analyte in the bodily fluid sample applied to the dual-chamber, multi-analyte test strip.

Test meter 200 is configured such that the third electrical connector contacts the first counter/reference contact pad of the test strip in an opposing manner with respect to the contact of the fourth electrical connector and the second counter/reference contact pad. In other words and as depicted in FIGS. 4A and 4B, the third electrical contact makes contact from the bottom side of the test strip and the fourth electrical contact makes contact from the top side of the test strip. In addition, the first electrical connector is configured to contact the first analyte contact pad of the test strip in an opposing manner with respect to the contact of the second electrical connector with the second analyte contact pad of the test strip. These opposing contact configurations provide for the test meter to be beneficially small in size while still providing the electrical connections necessary for operation of the test meter with to a dual chamber, multi-analyte test strip. These configurations also minimize the mechanical complexity of the test meter while providing for connection to the test strip.

In the embodiment of FIGS. 4A and 4B, signal processing module 204 includes, for example, a signal receiving component, a signal measurement component, a processor component and a memory component (each not shown in FIGS. 4A and 4B). Test meter 200 can measure, for example, electrical resistance, electrical continuity or other electrical characteristic between a first working electrode and a first counter/reference electrode layer and between a second working electrode and a second counter/reference electrode layer. One skilled in the art will appreciate that the test meter 200 can also employ a variety of sensors and circuits that are not depicted in simplified FIG. 4A during determination of a first analyte and a second analyte.

Successful operation of a dual chamber, multi-analyte test strip according to an embodiment of the present invention was verified as follows. The dual chamber, multi-analyte test strip was manufactured from the following materials:

First and second insulating layers and counter/reference insulating layer—Polyester Film with a thickness of ~178 μm (commercially available under the trade name Melinex 329 from Dupont Teijin Films, Hopewell, Va., USA);

First and second conductive layers—Palladium

First and second counter/reference layers—Gold

First and second patterned spacer layers—Approximately 95 μm total thickness (consisting of an approximately 50 um thick PET layer that is coated on both major surfaces with an approx. 22.5 um thick thermoplastic heat activated adhesive)

First analyte reagent layer (for glucose determination):
100 mM Tris Buffer, pH 7.4;
% w/v Hydroxyethyl cellulose;
10% w/v Potassium Hexacyanoferrate (III);
1% w/v Glucose Oxidase.

Second analyte reagent layer (for ketone determination)
100 mM Tris Buffer, pH 7.4;
% w/v Hydroxyethyl cellulose;
10% w/v Potassium Hexacyanoferrate (III);
1% w/v Hydroxybutyrate Dehydrogenase
1% w/v Diaphorase.

A dual chamber, multi-analyte test strip was manufactured using conventional thermal lamination and reagent layer application and drying techniques. The resulting test strip was tested on a standard bi-potentiostat. Reference and counter electrodes of the bi-potentiostat were connected to the first and second counter/reference contact pads of the test strip. The working electrodes of the bi-potentiostat were connected to the first and second analyte contact pads of the test strip. The connections were made in a manner electrically equivalent to that depicted in FIG. 4A.

Figure 5:
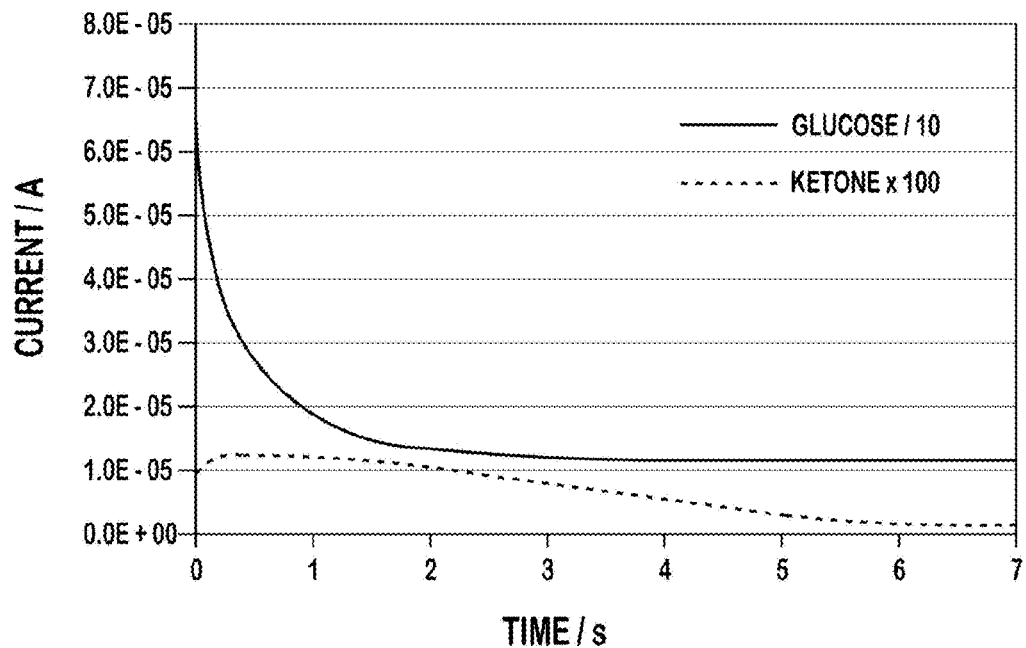
FIG. 5 is a graph of current (in amps) versus time (in seconds) obtained during testing of a dual-chamber, multi-analyte test strip according to an embodiment of the present invention.
Figure 6:
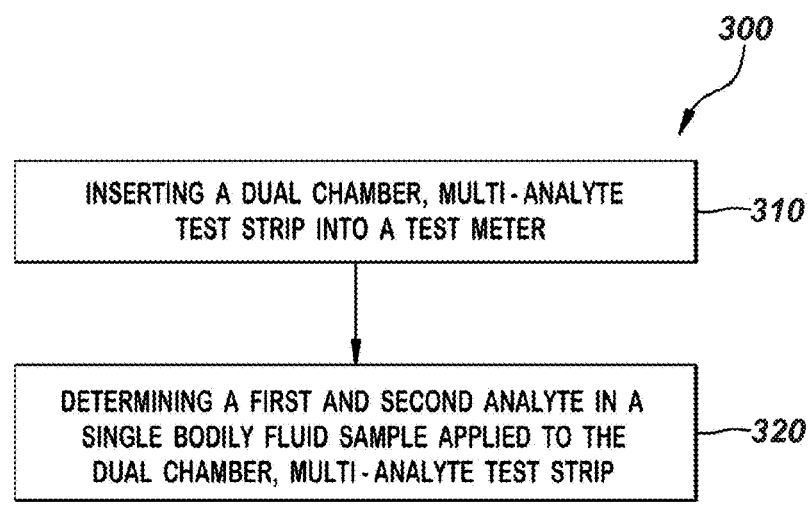
FIG. 6 is a flow diagram depicting stages in a process for determining multiple analytes in a single bodily fluid sample applied to a dual-chamber, multi-analyte test strip according to an embodiment of the present invention

A glucose and ketone standard solution was applied to the dual chamber, multi-analyte test strip. Following a 3 second preconditioning sequence (equivalent to an open circuit being applied to the test strip for 3 seconds), a potential of 0.4V was applied to the test strip for seven seconds. FIG. 5 shows the current output for the dual chamber, multi-analyte test strip for the duration of the 0.4V applied potential. FIG. 6 indicates that a sufficiently stable current is generated for control solution sample that has entered both the first and second sample-receiving chambers of the test strip, indicating that the test strip can be successfully employed for the detection of both glucose and ketone and that there was no apparent cross contamination in either determination.

FIG. 6 is a flow diagram depicting stages in a method 300 for determining multiple analytes (for example, the analyte glucose and the ketone analyte 3-hydroxybutyrate) in a single bodily fluid sample (such as a whole blood sample) applied to a dual chamber, multi-analyte test strip according to an embodiment of the present invention.

At step 310 of method 300, a dual chamber, multi-analyte test strip is inserted into a test meter. The insertion of the test strip into the meter is such that (i) a first electrical connector of the test meter comes into contact with a first analyte contact pad of a first working electrode of the test strip; (ii) a second electrical connector of the test meter comes into contact with a second analyte contact pad of a second working electrode of the test strip; (iii) a third electrical connector of the test meter comes into contact with a first counter/reference electrode contact pad of the test strip; and (iv) a fourth electrical connector of the test meter comes into contact with a second counter/reference electrode contact pad of the test strip.

The method also includes determining at least a first analyte and a second analyte in a single bodily fluid sample applied to test strip using a signal processing module of the test meter (see step 320 of FIG. 5), the single bodily fluid sample having entered a first sample-receiving chamber and a second sample-receiving chamber of the dual chamber, multi-analyte test strip following application of the bodily fluid sample thereto.

During the determining step, the signal processing module receives a first signal via the first electrical connector and the third electrical connector and employs the first signal for the determination of the first analyte. During the determination step, the signal processing module also receives a second signal via the second electrical connector and the fourth electrical connector and employs the second signal for the determination of the second analyte. In method 300, the first counter/reference electrode layer is configured in an opposing relationship to the first working electrode; and the second counter/reference electrode layer is configured in an opposing relationship to the second working electrode.

Once apprised of the present disclosure, one skilled in the art will recognize that method 300 can be readily modified to incorporate any of the techniques, benefits and characteristics of dual chamber, multi-analyte test strips according to embodiments of the present invention and described herein, as well as those of test meters according to embodiments of the present invention described herein. Moreover, the bodily fluid sample can be applied to the dual chamber, multi-analyte test strip either before the inserting step or after the inserting step.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A test meter for use with a dual-chamber, multi-analyte test strip, the test meter comprising:
    a test strip receiving module with:
        a first electrical connector configured for contacting a first analyte contact pad of a first working electrode of the dual-chamber, multi-analyte test strip;
        a second electrical connector configured for contacting a second analyte contact pad of a second working electrode of the dual-chamber, multi-analyte test strip
        a third electrical connector configured for establishing an operational electrical contact to a first counter/reference contact pad of a first counter/reference electrode layer of the dual-chamber, multi-analyte test strip; and
        a fourth electrical connector configured for establishing an operational electrical contact to a second counter/reference contact pad of a second counter/reference electrode layer of the dual-chamber, multi-analyte test strip; and
    a signal processing module,
    wherein the signal processing module is configured to receive a first signal via the first electrical connector and the third electrical connector and employ the first signal for the determination of a first analyte in a bodily fluid sample applied to the dual-chamber, multi-analyte test strip; and
    wherein the signal processing module is also configured to receive a second signal via the second electrical connector and fourth electrical connector and employ the second signal for the determination of a second analyte in the bodily fluid sample applied to the dual-chamber, multi-analyte test strip, and
    wherein the third electrical connector is configured to contact the first counter/reference contact pad in an opposing manner with respect to the contact of the fourth electrical connector and the second counter/reference contact pad; and
    wherein the third electrical connector and the fourth electrical connector are in an opposing configuration, and
    wherein the test strip receiving module is configured for operationally receiving a multi-analyte test strip with:
        a first insulating layer;
        a first electrically conductive layer disposed on the first insulating layer, the electrically conductive layer including the first working electrode with the first analyte contact pad;
        a first patterned spacer layer positioned above the first electrically conductive layer, the patterned spacer layer defining a first sample-receiving chamber therein that overlies the first working electrode, the first sample-receiving chamber having a first end opening and a second end opening;
        a first counter/reference electrode layer overlying and exposed to the first sample receiving chamber, the first counter/reference electrode layer configured in an opposing relationship to the first working electrode and having the first counter/reference contact pad;
        a counter/reference insulating layer disposed over the first counter/reference electrode layer,
        a second counter/reference electrode layer disposed over the counter/reference insulating layer the second counter/reference electrode layer having the second counter/reference contact pad,
        a second patterned spacer layer positioned above the second counter/reference electrode layer, the second patterned spacer layer defining a
        second sample-receiving chamber therein with a first end opening and a second end opening;
        a second electrically conductive layer disposed above the second patterned spacer layer, the second electrically conductive layer including the second working electrode with the second analyte contact pad;
        a second insulating layer disposed above the second electrically conductive layer;
        a first analyte reagent layer disposed on at least a portion of the first working electrode within the first sample-receiving chamber; and
        a second analyte reagent layer disposed on at least a portion of the second working electrode within the second sample-receiving chamber;
    wherein the second sample-receiving chamber overlies the second working electrode, and
    wherein the second counter/reference electrode layer is exposed to the second sample receiving chamber and configured in an opposing relationship to the second working electrode.

2. The test meter of claim 1 wherein first electrical connector is configured to contact the first analyte contact pad in an opposing manner with respect to the contact of the second electrical connector with the second analyte contact pad.

3. The test meter of claim 1 wherein the first analyte is non-identical in comparison to the second analyte.

4. The test meter of claim 3 wherein the first analyte is glucose.

5. The test meter of claim 4 wherein the second analyte is a ketone.

6. The test meter of claim 5 wherein the ketone is 3-hydroxybutyrate.

7. The test meter of claim 1 wherein the bodily fluid sample is a whole blood sample.

8. The test meter of claim 1 wherein the signal processing module is configured for determination of the first analyte and determination of the second analyte via an electrochemical-based determination technique.

9. The test meter of claim 1 wherein the signal processing module is configured to receive the first signal and the second signal in a sequential manner.

10. The test meter of claim 1 wherein the signal processing module is configured to receive the first signal and the second signal in a simultaneous manner.

* * * * *